US006167000A

United States Patent [19]

Chow

[11] Patent Number: 6,167,000

[45] Date of Patent: Dec. 26, 2000

[54] MULTIPLE TIMER DISPLAY

[76] Inventor: Shiou-Sheng Chow, No. 22, Alley 15, Lane 151, Chung-Shan Rd. Sec. 2, Shu-Lin Chen, Taipei Hsien, Taiwan

[21] Appl. No.: 09/175,335

[22] Filed: Oct. 20, 1998

[51] Int. Cl.[7] .............................. G04F 10/00; A01H 3/34

[52] U.S. Cl. ............................ 368/107; 368/10; 307/141; 307/141.4

[58] Field of Search .............................. 368/10, 107, 113, 368/84, 242; 307/141, 141.4

[56] References Cited

U.S. PATENT DOCUMENTS

| | | | |
|---|---|---|---|
| 4,367,527 | 1/1983 | desjacques | 368/107 |
| 5,666,331 | 9/1997 | kollin | 368/245 |
| 5,699,320 | 12/1997 | wan | 368/10 |
| 5,854,774 | 12/1998 | timme | 368/10 |
| 6,011,755 | 1/2000 | mulhall et al. | 368/10 |

*Primary Examiner*—Bernard Roskoski
*Attorney, Agent, or Firm*—Bacon & Thomas, PLLC

[57] ABSTRACT

A multiple timer device includes a DC power supply circuit, a central processing unit, a slide switch, a function key set, and a liquid crystal multiple display. The slide switch serves to select an operating mode according to settings programmed by pressing the function keys, so that the central processing unit will activate the electromagnetic switch at preprogrammed times, which in turn will connect the AC power source with an output socket. The liquid crystal multiple display is composed of a digital display and a clock hand display. Arranged in a circle around the clock hand display are a plurality of display timing areas for digitally displaying, in relation to the clock hands, the programmed starting times.

3 Claims, 2 Drawing Sheets

MULTIPLE TIMER DISPLAY

BACKGROUND OF THE INVENTION

The invention relates to a multiple timer display device, and particularly to a liquid crystal display of a timer device, composed of a digital display and a needle display. On the needle display in a circular arrangement are a number of timing display areas that will digitally display the programmed starting times.

Conventionally, a regular timer involves a turning disc on its control panel. The turning disc will rotate With the timer, and on the turning disc are a number of pins that can be inserted in optional locations. The timer is a socket and a power supply plug. The power plug can be plugged to an indoor AC power outlet, and then an electrical appliance to be activated at a specific time maybe plugged into the timer's socket, after which the inserting pins are inserted to the time locations to start operation. When the turning disc has rotated to the position of a pin, the electromagnetic switch inside the timer will be turned on, so power is connected to the socket and power source, to activate the electrical appliance according to the programmed time schedule.

Besides, there is another type with a number of timing push keys in circular arrangement on the turning disc. The timing push keys are pushed to set the starting times, to program the starting times in a way similar to the aforementioned model.

The above two models of timer are mechanical, and since mechanical time setting is not precise, its setting can only be operated within a short cycle of 24 hours, so it is impossible to set the time for the next day, or any day within the week. Therefore, the setting of a time in a longer cycle will rely on an electronic timer, since an electronic timer is set by programming desired operating schedules in any day in the next several days, it has a greater flexibility in application.

A conventional electronic timer, however, has only one liquid crystal digital display, which displays only the preset time and week, instead of displaying the programmed time schedules for the current day. If the user wishes to know the programmed schedules for the current day, he has to use the function keys on the time and check the times that have been programmed, so it is inconvenient in application.

Since the length of programmed operating times is known only to the person who has set the programmed schedules, other persons will not be able to know how long the time is remaining before it stops to operate, even the original person who has set the programs may forget his original settings after an extended period of use, and therefore, there is no way of knowing the duration of the operation once the preset time schedule is activated; this is a shortcoming that need to be addressed The liquid crystal display of a conventional electronic timer will display only a digital time, instead of a hand or needle indicated time (i.e., an analog-type clock face display), even though since everyone has a different way of knowing the time, some being used to see a digital display while others are used to see are the analog display, with most users being used to looking at a clock hand indication showing the time. Because the conventional electronic timer usually displays only a digital time, therefore, to a user who is used looking at a clock hand indicated time has to convert the digital display to an image of needles indicating the time, causing inconvenience to the user.

The inventor has considered the shortcomings of conventional electronic timers, such as: mere display of time without displaying the programmed starting time for the current day, inability to display the time remaining after the appliance is operated, single display of digital time without the analog clock face or clock hand display etc., therefore, such inconveniences in application need to be addressed. The inventor has devoted much research effort to design; a type of multiple timer display, comprising a DC supply circuit, a central processing unit, a slide switch, a function key set and a liquid crystal multiple display, the DC supply circuit being connected to an AC power to convert AC to DC for the purpose of supplying power to interior circuit, and said slide switch, function key set and liquid crystal multiple display being connected to the central processing unit. The slide switch serves to switch to the mode for operation, and the function keys serve to set the program schedules, so the central processing unit will activate the electromagnetic switch according to the programmed schedules, which in turn connect the AC power source with the output socket. The liquid crystal multiple display is composed of a digital display and a needle indicator display, and, in circular arrangement on the needle indicator display are a number of timing display areas, so it will digitally display the programmed starting times and will begin a countdown after the programmed schedule is activated, displaying the time remaining in the operation. Meanwhile, it displays the number of programmed sets on the current day when the timer is not activated, therefore it is quite convenient to the user.

SUMMARY OF THE INVENTION

The primary objective of the present invention is to present a liquid crystal multiple display for a timer, composed of a digital display and a needle indicator display, and a circular arrangement on the needle indicator display on which are a number of timing display areas, to digitally display the programmed starting times.

Another objective of the invention is to present a liquid crystal multiple display for timer, composed of a digital display and a clock hand display, in which the digital display will begin a countdown once the operation is activated, to display the time remaining after the operation, and will also display the number of programmed schedules on the current day when the timer is not activated, which is quite convenient to the user.

To enable better understanding of the invention, the following drawings are described in details.

DETAILED DESCRIPTION OF PREFERRED EMBODIMENT

Figure 1:
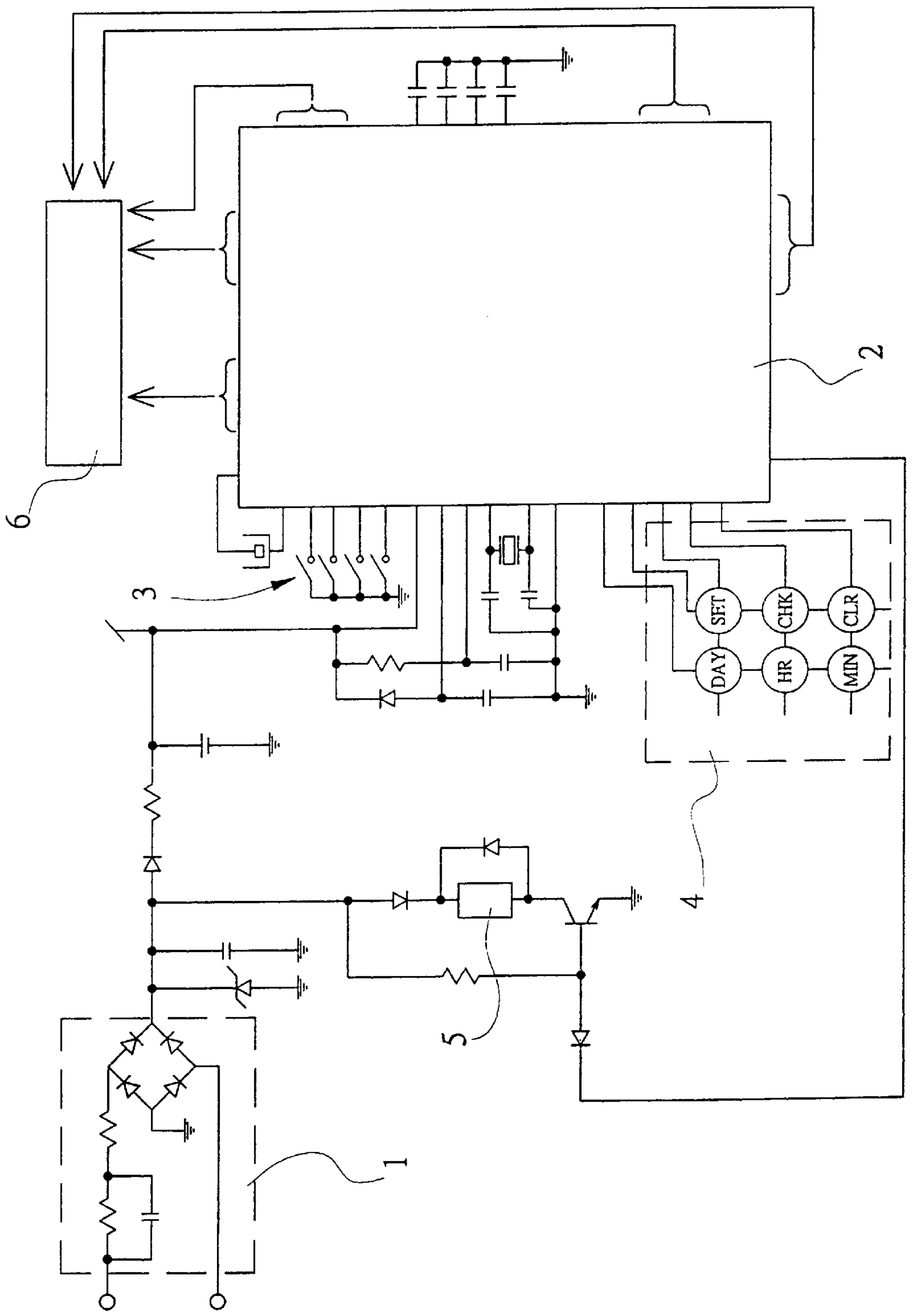
FIG. 1 is a circuit diagram of the invention.
Figure 2:
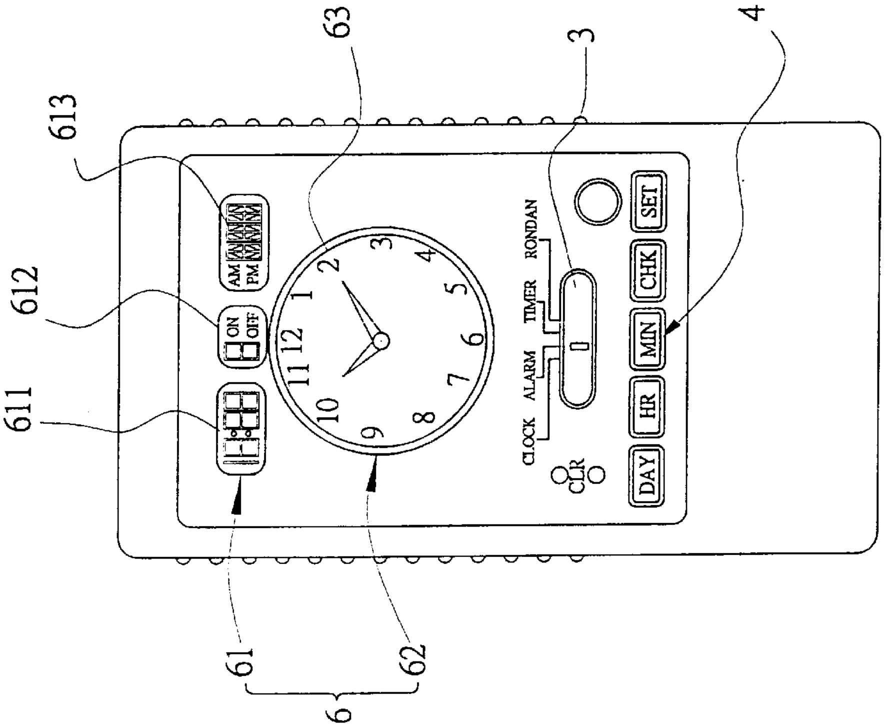
FIG. 2 is a front view of the invention in application.
Figure 3:
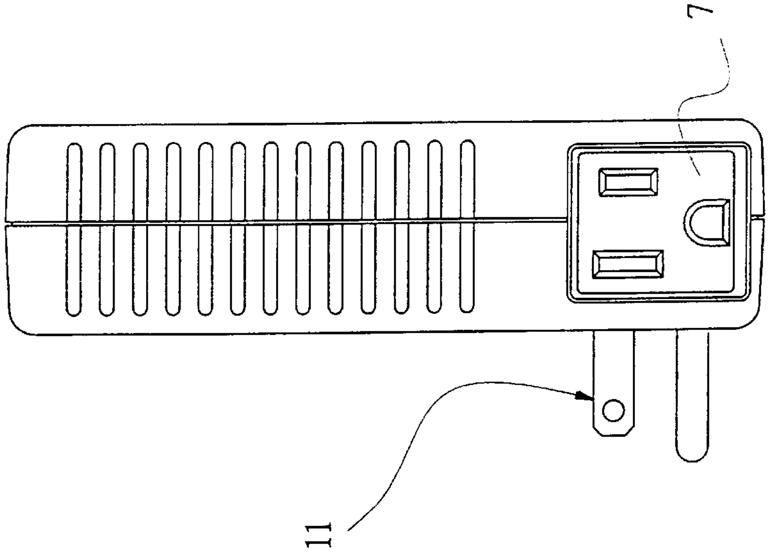
FIG. 3 is a section view of the invention in application.

Firsts referring to FIGS. 1, 2 and 3, the invention is mainly composed of the following components, which are described below:

a DC power supply circuit 1, connected to an AC plug 11, to convert AC to DC for the purpose of supplying power to interior circuitry;

a central processing unit 2, to be activated by a timer and programming;

a slide switch 3, connected to the central processing unit 2, said slide switch 3 serving to switch to the mode to be operated;

a function key set 4, connected to the central processing unit 2, said function keys 4 serving to operate the functions under the mode determined by the slide switch 3;

an electromagnetic switch 5, its electromagnetic unit connected to the central processing unit 2, the contact points (not shown in drawing) at two conducting sides of the electromagnetic switch 5 being connected respectively to an AC power source and an output socket 7;

a liquid crystal multiple display 6, connected to the central processing unit 2, said multiple display 6 being composed of a digital display 61 and a clock hand display 62, said digital display 61 being composed of a time display 611, a status display 612 and a week display 613 on the clock hand display 62 are a number of time display areas 63 arranged in a circle around said clock hand display at positions corresponding to numbers on a clock face, to enable digital display of the preset starting time. The time display area 63 will flash a blackened block at the appropriate one of the display areas 63 corresponding to the preset starting time to indicate when the electromagnetic switch 5, will be activated to connect the AC power source and the output socket to achieve the purpose of starting its performance.

With the aforementioned construction, the slide switch 3 can be pushed to select the mode to be operated, switching to set the CLOCK, ALARM, TIMER or RANDOM function, and by pressing the function keys 4, the present time, alarm, starting time and other functions can be programmed in the central processing unit 2.

In case the TIMER has been programmed to operate on every weekday for a certain period of time, said central processing unit 2 will command the operation according to the programmed schedule, activating the electromagnetic switch 5 to conduct the AC power source and the output socket 7, so that the electrical appliance connected to the output socket 7 will start to operate at the preset time.

The status display 612 of the digital display 61 of said multiple liquid crystal display 6 will display the number of sets to be executed on the current day. For example, if several starting times have been preset in sequence to operate on the current day, the digital display 61 will show the numbers of the programmed sets, such as: "1", "2", "3", etc.; the timing display areas 63 on the clock hand display 62 of said multiple liquid crystal display 6 will display the programmed time sections in the morning or afternoon (12 hours) of the current day, so the user may easily see how many sets of starting time are programmed in the morning or afternoon, and how many sets have been executed on the status display 612 in the digital display 61. Meanwhile, the programmed sections that have been executed will no longer be displayed in the timing display areas 63 in circular arrangement on the clock hand display 62, so the user can easily know the situation.

When one set is executed on the current day, said status display 612 will automatically switch to show its countdown status, so the user can know the time remaining in the programmed set.

Since said multiple liquid crystal display 6 is composed of the digital display 61 and the clock hand display 62, there will be simultaneous display of digital time and needle-indicated time, so the user have the option to see either display, which is an added convenience in application.

Because said multiple liquid crystal display 6 displays simultaneously the digital time, clock hand-indicated time, the number of programmed sets and the timed starting sections, there is an added convenience in application.

What is claimed is:

1. A timer having multiple displays, comprising:

a DC power supply circuit connected to an AC plug for converting AC power supplied by said AC plug into DC power;

a central processing unit connected to said DC power supply circuit and arranged, when in a programmed mode, to be activated by a timer in order to control an electromagnetic switch having contact points connected respectively to the AC plug and an AC socket, and thereby to supply power from said AC plug to the AC socket according to programmed schedules;

a slide switch connected to the central processing unit, said slide switch serving to switch the central processing unit to the programmed mode;

a function key set connected to the central processing unit, function keys of said function key set serving to set programs when the central processing unit is switched to a programming mode by the slide switch; and a liquid crystal multiple display connected to the central processing unit, said multiple display including a digital display and a clock hand display, said digital display being composed of a time display, a status display, and a week display, wherein a plurality of timing display areas are arranged in a circle around said clock hand display at positions corresponding to positions of numbers on a clock face, and wherein selected ones of said timing display areas at positions corresponding to said programmed starting times will indicate the programmed starting times, so that the programmed starting times are indicated by both said digital display and also by said selected ones of said timing display areas around said clock hand display.

2. A multiple display timer as claimed in claim 1, wherein said selected ones of said timing display areas will flash to indicate the programmed starting times.

3. A multiple display timer as claimed in claim 2, wherein said selected ones of said timing display areas cease to flash when respective programmed starting times have passed.

* * * * *